(12) United States Patent
Hodgson et al.

(10) Patent No.: US 6,258,936 B1
(45) Date of Patent: Jul. 10, 2001

(54) SPOIIIE

(75) Inventors: John Edward Hodgson, Malvern; Alison Frances Chalker, Collegeville, both of PA (US)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/205,048

(22) Filed: Dec. 4, 1998

Related U.S. Application Data

(62) Division of application No. 08/785,431, filed on Jan. 17, 1997, now Pat. No. 5,891,667.

(30) Foreign Application Priority Data

Jan. 17, 1996 (GB) .................................................. 9600955

(51) Int. Cl.⁷ ............................. C07K 1/00; C07K 14/00; C12P 21/06; C12P 21/04; C12N 1/00
(52) U.S. Cl. ......................... 530/350; 530/820; 530/825; 435/69.1; 435/69.7; 435/71.1; 435/243; 435/252.1; 435/252.3
(58) Field of Search ..................................... 530/350, 820, 530/825; 435/69.1, 243, 252.1, 252.3, 69.7, 71.1

(56) References Cited

PUBLICATIONS

Herzog et al DNA and Cell Biology 12(6):465–471, 1993.*
Rudinger et al. "Peptide Hormones" pp. 1–7 University Park Press, Jun. 1976.*
Burgess et al. J Cell Biol 111:2129–2138, 1990.*

* cited by examiner

*Primary Examiner*—Mark Navarro
*Assistant Examiner*—Li Lee
(74) *Attorney, Agent, or Firm*—Edward R. Gimmi; Thomas S. Deibert; William T. King

(57) ABSTRACT

The invention provides spoIIIE polypeptides and DNA (RNA) encoding spoIIIE polypetides and methods for producing such polypeptides by recombinant techniques. Also provided are methods for utilizing spoIIIE polypeptide for the protection against infection, particularly bacterial infections.

12 Claims, 4 Drawing Sheets

FIGURE 1. spoIIIE cloned DNA sequence [SEQ ID NO:1 and SEQ ID NO:3]

```
  1 ttggctcaag caaaaaagaa atcgacagct aagaaaaaaa cagCATCAAA
 51 AAAAGAACA AATTCAAGGA AAAAGAAGAA TGATAATCCG ATACGTTATG
101 TCATAGCTAT TTTAGTAGTT GTATTAATGG TGTTGGGTGT TTTCCAATTA
151 GGAATAATCG GTCGTCTAAT TGACAGCTTC TTTAATTATT TATTGGGTA
201 CAGTAGATAT TTAACATATA TTTTAGTACT CTTAGCAACT GGTTTTATTA
251 CATACTCTAA ACGTATTCCT AAAACTAGAC GAACGGCTGG TTCGATTGTA
301 TTGCAAATTG CATTGCTATT TGTATCACAG TTAGTTTTTC ATTtaatag
351 tGGTATCAAA GCTGAAAGAG AACCTGTACT TTCTTATGTA TATCAGTCAT
401 ACCAACACAG TCATTTTCCA AATTTGGTG GCGGTGTATT AGTTTTTAT
451 TTATTAGAGT TAAGCGTaCC TTTAATTCA TTATTGGTG TATGTATTAT
501 TACTATTTA TTTATTATGT CAAGTGTTAT TTTATTAACA AACCATCAAC
551 ATCGTGATGT TGCAAAAGTT GCACTGGAAA ATATAAAAGC TTGGTTTGGT
601 TCATTTAATG AAAAAATGTC GGAAAGAAAC CAAGAAAAAC AATTGAAGCG
651 TGAAGAAAAA GCGAGACTTA AAGAAGAACA AAAGGCACGT CAAAATGAAC
701 AGCCACAAAT AAAAGATGTG AGTGATTTTA CGGAAGTGCC TCAAGAAAGA
751 GATATTCCAA TTTATGGGCA TACTGAAAAT GAAAGTAAAA GCCAGTGTCA
801 ACCAAGTCGA AAAAAACGAG TGTTTGATGC AGAGAATAGT TCGAATAACA
```

Figure 1A

```
 851  TCGTAAATCA TCAAGCAGAT CAGCAAGAGC AATTAACAGA ACAAACTCAT
 901  AACAGTGTTG AAAGTGAAAA CACTATTGAA GAAGCTGGTG AAGTACGAA
 951  TGTATCGTAT GTTGTTCCAC CGTTAACTTT ACTTAATCAA CCTGCAAAAC
1001  AAAAAGCAAC ATCTAAAGCT GAAGTACAAC GTAAAGGACA AGTACTAGAG
1051  AATACATTAA AAGATTTGG GGTAAATGCA AAAGTGACAC AAATTAAAAT
1101  TGGTCCTGCA GTAACTCAAT ATGAAATTCA ACCAGCTCAA GGGGTTAAAG
1151  TGAGTAAAAT TGTAAACTTG CATAATGATA TTGCATTAGC TTTAGCAGCA
1201  AAAGATGTTA GAATCGAAGC ACCAATACCT GGTCGCTCTG CAGTAGGTAT
1251  TGAAGTGCCA AATGAGAAAA TTTCATTAGT TTCACTAAAA GAAGTTTTAG
1301  ATGAAAAATT CCCGTCTAAT AATAAACTAG AAGTTGGATT AGGAAGAGAT
1351  ATATCAGGTG ATCCAATTAC TGTTCCACTA AATGAAATGC CACACTTATT
1401  GGTGGCAGGA TCGACGGGTA GTGGTAAATC TGTTTGTATA AATGGTATTA
1451  TTACAAGTAT TTTATTAAAT GCTAAGCCGC ATGAAGTTAA ACTTATGTTA
1501  ATCgATCCGA AAATGGTTGA ACTAAATGTT TATAACGgaa ttcCACATTT
1551  ATTAATTCCG GTTGTTACAA ATCCCTCaTAA AGCTGCTCAA GCTTAGAAA
1601  AAATTGTAGC TGAGATGGAA AGACGTTATG ATTTATTCCA ACATTCATCA
1651  ACTAGAAATA TTAAAGGTTA TAACGAATTA ATCCGTAAGC AAAATCAAGA
```

Figure 1B

```
1701  ATTAGATGAG AAGCAACCAG AATTACCTTA TATCGTTGTT ATTGTAGATG
1751  AGCTTGCAGA TTTAATGATG GTAGCTGGTA AAGAAGTTGA AAATGCGATT
1801  CAACGTATCA CACAAATGGC ACGTGCAGCA GGTATACATT TGATTGTAGC
1851  AACACAAAGA CCTTCTGTGG ATGTAATTAC AGGTATCATT AAAAATAACA
1901  TTCCATCTAG AATTGCTTTT GCTGTGAGTT CTCAAACAGA TTCAAGAACT
1951  ATTATTGGTA CTGGCGGCGC AGAAAAGTTA CTGGTAAAG GTGACATGTT
2001  ATACGTTGGA AATGGTGATT CATCACAAAC ACGTATTCAA GGGGCGTTTT
2051  TAAGTGACCA AGAGGTGCAA GATGTTGTAA ATTATGTAGT AGAACAACAA
2101  CAGGCAAATT ATGTAAAAGA AATGGAACCA GATGCACCAG TGGATAAATC
2151  GGAAATGAAA AGTGAAGATG CTTTATATGA TGAAGCGTAT TTGTTTGTTG
2201  TTGAACAACA AAAGGCAAGT ACATCATTGT TACAACGCCA ATTAGAATT
2251  GGTTATAATA GAGCATCTAG GTTGATGGAT GATTAGAAAC GCAATCAGGT
2301  AATCGGTCCA CAAAAGGAA GCAAGCCTAG ACAAGTTTTA ATAGATCTTA
2351  ATAATGACGA GGTGTAA
```

FIGURE 2. spoIIIE deduced amino acid sequence [SEQ ID NO:2 and SEQ ID NO:4]

```
  1  LAQAKKKSTA KKKTASKKRT NSRKKKNDNP IRYVIAILVV VLMVLGVFQL
 51  GIIGRLIDSF FNYLFGYSRY LTYILVLLAT GFITYSKRIP KTRRTAGSIV
101  LQIALLFVSQ LVFHFNSGIK AEREPVLSYV YQSYQHSHFP NFGGGVLGFY
151  LLELSVPLIS LFGVCIITIL LLCSSVILLT NHQHRDVAKV ALENIKAWFG
201  SFNEKMSERN QEKQLKREEK ARLKEEQKAR QNEQPQIKDV SDFTEVPQER
251  DIPIYGHTEN ESKSQCQPSR KKRVFDAENS SNNIVNHQAD QQEQLTEQTH
301  NSVESENTIE EAGEVTNVSY VVPPLTLLNQ PAKQKATSKA EVQRKGQVLE
351  NTLKDFGVNA KVTQIKIGPA VTQYEIQPAQ GVKVSKIVNL HNDIALALAA
401  KDVRIEAPIP GRSAVGIEVP NEKISLVSLK EVLDEKFPSN NKLEVGLGRD
451  ISGDPITVPL NEMPHLLVAG STGSGKSVCI NGIITSILLN AKPHEVKLML
501  IDPKMVELNV YNGIPHLLIP VVTNPHKAAQ ALEKIVAEME RRYDLFQHSS
551  TRNIKGYNEL IRKQNQELDE KQPELPYIVV IVDELADLMM VAGKEVENAI
601  QRITQMARAA GIHLIVATQR PSVDVITGII KNNIPSRIAF AVSSQTDSRT
651  IIGTGGAEKL LGKGDMLYVG NGDSSQTRIQ GAFLSDQEVQ DVVNYVVEQQ
701  QANYVKEMEP DAPVDKSEMK SEDALYDEAY LFVVEQQKAS TSLLQRQFRI
751  GYNRASRLMD DLERNQVIGP QKGSKPRQVL IDLNNDEV
```

SPOIIIE

This is a divisional of application Ser. No. 08/785,431, filed Jan. 17, 1997 now U.S. Pat. No. 5,891,667.

FIELD OF THE INVENTION

This invention relates to newly identified polynucleotides and polypeptides, and their production and uses, as well as their variants, agonists and antagonists, and their uses. In particular, in these and in other regards, the invention relates to polynucleotides and polypeptides of the spo family, hereinafter referred to as "spoIIIE".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

SpoIIIE is a membrane bound protein involved in chromosome partitioning during sporulation and vegetative replication in a wide variety of bacteria. The SpoIIIE gene was initially characterised in *Bacillus subtilis* (Butler P. D. and Mandelstam J. (1987) Journal of General Microbiology 133:2359–2370). SpoIIIE protein has an ATP binding site and is membrane-bound, and appears to form a pore in the nascent spore septum, through which the prespore chromosome is driven in a conjugation-like mechanism (Wu L. J., Lewis P. J., Allmansberger R., Hauser P. M. and Errington J. (1995) Genes and Development 9:1316–1326). spoIIIE mutants cannot sporulate as they are unable to partition the prespore chromosome into the polar prespore compartment. Instead a specific chromosomal segment comprising approximately 30% of the chromosome enters the prespore, while the rest remains in the mother cell, trapped by the septum (Wu L. J. and Errington J. (1994) Science 264:572–575). In wild-type cells SpoIIIE is membrane-bound, and appears to form a pore in the nascent spore septum, through which the prespore chromosome is driven in a conjugation-like mechanism (Wu L. J., Lewis P. J., Allmansberger R., Hauser P. M. and Errington J. (1995) Genes and Development 9:1316–1326).

It has been shown that SpoIIIE is also required for correct partitioning of the *B.subtilis* chromosome during vegetative cell division. spoIIIE- Mutants in which replication has been artificially delayed are unable to separate the replicated chromosomes before septum formation, resulting in a trapped nucleoid similar to that formed at the start of sporulation (Sharpe M. E. and Errington J. (1995) Proceedings of the Natural Academy of Sciences USA 92:8630–8634).

SpoIIIE has been shown to be essential in *Escherichia coli* (Begg K. J., Dewar, S. J. and Donachie W. D. (1995) Journal of Bacteriology 177:6211–6222). Highly conserved SpoIIIE homologues are found in diverse members of the eubacteria such as *Campylobacter jejuni* (Miller, S., Pesci E. C. and Pickett C. L. (1994) Gene 146:31–38), *Coxiella burnetii* (Oswald W. and Thiele D. (1993) Journal of Veterinary Medecine B40:366–370), *Eshcerichia coli* (Begg 1995 above) and *Haemophilus influenzae* (Fleischmann, R. D., Adams, M. D., White, O., Clayton, R. A., Kirkness, E. F., Kerlavage, A. R., Bult, C. J., Tomb, J.-F., Dougherty, B. A., Merrick, J. M., McKenney, K., Sutton, G., FitzHugh, W., Fields, C. A., Gocayne, J. D., Scott, J. D., Shirley, R., Liu, L.-I., Glodek, A., Kelley, J. M., Weidman, J. F., Phillips, C. A., Spriggs, T., Hedblom, E., Cotton, M. D., Utterback, T. R., Hanna, M. C., Nguyen, D. T., Saudek, D. M., Brandon, R. C., Fine, L. D., Fritchman, J. L., Fuhrmann, J. L., Geoghagen, N. S. M., Gnehm, C. L., McDonald, L. A., Small, K. V., Fraser, C. M., Smith, H. O. and Venter, J. C. (1995) Science 269:496–512). All of these proteins are 36–55% identical at the amino acid level overall. Their N-terminal 200 amino acids are hydrophobic and not conserved, so if the C-terminal 500 or so amino acids are considered alone the level of conservation rises to 42–67% identical amino acids. This high level of identity among diverse eubacteria strongly suggests commonality of function.

Inhibitors of SpoIIIE proteins would prevent the bacterium from establishing and maintaining infection of the host by preventing it from correctly partitioning the chromosome in the manner described above and thus arresting cell division and growth, rendering the bacterium susceptible to host defences and leading ultimately to cell death and thereby have utility in anti-bacterial therapy.

Clearly, there is a need for factors that may be used to screen compounds for antibiotic activity and which factors may also be used to determine their roles in pathogenesis of infection, dysfunction and disease. There is also a a need for identification and characterization of such factors and their antagonists and agonists which can play a role in preventing, ameliorating or correcting infections, dysfunctions or diseases.

The polypeptides of the invention have amino acid sequence homology to a known *B. subtilis* spoIIIE protein.

SUMMARY OF THE INVENTION

It is an object of the invention to provide polypeptides that have been identified as novel spoIIIE polypeptides by homology between the amino acid sequence set out in FIG. 2 and a known amino acid sequence or sequences of other proteins such as *B. subtilis* spoIIIE protein.

It is a further object of the invention to provide polynucleotides that encode spoIIIE polypeptides, particularly polynucleotides that encode the polypeptide herein designated spoIIIE.

In a particularly preferred embodiment of this aspect of the invention the polynucleotide comprises a region encoding spoIIIE polypeptides comprising the sequence set out in FIG. 1 [SEQ ID NO:1 and SEQ ID NO:3], or a variant thereof.

In another particularly preferred embodiment of the invention there is a novel spoIIIE protein from *Staphylococcus aureus* comprising the amino acid sequence of FIG. 2 [SEQ ID NO:2 and SEQ ID NO:4], or a variant thereof.

In accordance with this aspect of the invention there is provided an isolated nucleic acid molecule encoding a mature polypeptide expressible by the *Staphylococcus aureus* WCUH 29 strain contained in NCIMB Deposit No. 40771.

In accordance with this aspect of the invention there are provided isolated nucleic acid molecules encoding spoIIIE, particularly *Staphylococcus aureus* spoIIIE, including mRNAs, cDNAs, genomic DNAs. Further embodiments of this aspect of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of this aspect of the invention are naturally occurring alelic variants of spoIIIE and polypeptides encoded thereby.

In accordance with this aspect of the invention there are provided novel polypeptides of *Staphylococcus aureus* referred to herein as spoIIIE as well as biologically, diagnostically, prophylactically, clinically or therapeutically useful variants thereof, and compositions comprising the same.

Among the particularly preferred embodiments of this aspect of the invention are variants of spoIIIE polypeptide encoded by naturally occurring alleles of the spoIIIE gene.

In a preferred embodiment of this aspect of the invention there are provided methods for producing the aforementioned spoIIIE polypeptides.

In accordance with yet another aspect of the invention, there are provided inhibitors to such polypeptides, useful as antibacterial agents, including, for example, antibodies.

In accordance with certain preferred embodiments of this aspect of the invention, there are provided products, compositions and methods for (i) assessing spoIIIE expression, (ii) treating disease, for example, disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis), (iii) assaying genetic variation, (iv) and administering a spoIIIE polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to spoIIIE polynucleotide sequences, particularly under stringent conditions.

In certain preferred embodiments of this aspect of the invention there are provided antibodies against spoIIIE polypeptides.

In accordance with another aspect of the invention, there are provided spoIIIE agonists and antagonists each of which are also preferably bacteriostatic or bacteriocidal.

In a further aspect of the invention there are provided compositions comprising a spoIIIE polynucleotide or a spoIIIE polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1, 1A, 1B show the polynucleotide sequence of *Staphylococcus aureus* spoIIIE [SEQ ID NO:1 and SEQ ID NO:3]. The TTG start codon is shown in bold and underlined. The ATG start codon is shown italicized and underlined. The stop codon (UAA) is shown underlined.

FIG. 2 shows the amino acid sequence of *Staphylococcus aureus* spoIIIE [SEQ ID NO:2 and SEQ ID NO:4] deduced from the polynucleotide sequence of FIG. 1. Methionine number 43 is shown in bold.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods commonly employed to determine identity or similarity between sequences include, but are not limited to those disclosed in Carillo, H., and Lipman, D., SIAM *J. Applied Math.*, 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990)).

"Isolated" means altered "by the hand of man" from its natural state, i.e., if it occurs in nature, it has been changed or removed from its original environment, or both. For example, polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide (s)" includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques which are well known to the art. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains and the amino or carboxyl termini. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel spoIIIE polypeptides and polynucleotides as described in greater detail below. In particular, the invention relates to polypeptides and polynucleotides of a novel spoIIIE gene of *Staphylococcus aureus,* which is related by amino acid sequence homology to *B. subtilis* spoIIIE polypeptide. The invention relates especially to spoIIIE having the nucleotide and amino acid sequences set out in FIG. 1 and FIG. 2 respectively, and to the spoIIIE nucleotide sequences of the DNA in NCIMB Deposit No. 40771 and amino acid sequences encoded therin. The amino acid sequence of SEQ ID NO:2 AND SEQ ID NO:4 is the translated open reading frame sequence of SEQ ID NO:1 AND SEQ ID NO:3 and displays homology of 49% identity overall and 67% identity in the C-terminal conserved 500 amino acids to spoIIIE from *B. subtilis.* The deduced amino acid sequence is based upon the use of TTG as a start codon, however, another amino acid sequence embodiment of the invention is based on an ATG start codon, and a further embodiment is the DNA sequence of SEQ ID NO:1 AND SEQ ID NO:3 that encodes the amino acid sequence starting at Methionine number 43 of SEQ ID NO:2 AND SEQ ID NO:4. Thus, hererin, "SEQ ID NO:2 AND SEQ ID NO:4" means the amino acid sequence starting at Lysine number 1 or Methionine number 43. Also, herein, "SEQ ID NO:1 AND SEQ ID NO:3" means the polynucleotide starting at Thymine number 1 or Adenine number 127.

Techniques are available to evaluate temporal gene expression in bacteria, particularly as it applies to viability under laboratory and host infection conditions. A number of methods can be used to identify genes which are essential to survival per se, or essential to the establishment and/or maintenance of an infection. Identification of expression of a sequence by one of these methods yields additional information about its function and assists in the selection of such sequence for further development as a screening target. Briefly, these approaches include, for example:

1) Signature Tagged Mutagenesis (STM)

This technique is described by Hensel et al., *Science* 269: 400–403(1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

In *Staphylococcus aureus*, because the transposon system is less well developed, a more efficient way of creating the tagged mutants is to use the insertion-duplication mutagenesis technique as described by Morrison et al., *J. Bacteriol.* 159:870 (1984) the contents of which is incorporated by reference for background purposes.

2) In Vivo Expression Technology (IVET)

This technique is described by Camilli et al., *Proc. Nat'l. Acad. Sci. USA.* 91:2634–2638 (1994) and Mahan et al., *Infectious Agents and Diseases* 2:263–268 (1994), the contents of each of which is incorporated by reference for background purposes. IVET identifies genes up-regulated during infection when compared to laboratory cultivation, implying an important role in infection. Sequences identified by this technique are implied to have a significant role in infection establishment/maintenance.

In this technique random chromosomal fragments of target organism are cloned upstream of a promoter-less reporter gene in a plasmid vector. The pool is introduced into a host and at various times after infection bacteria may be recovered and assessed for the presence of reporter gene expression. The chromosomal fragment carried upstream of an expressed reporter gene should carry a promoter or portion of a gene normally upregulated during infection. Sequencing upstream of the reporter gene allows identification of the up regulated gene.

3) Differential Display

This technique is described by Chuang et al., *J. Bacteriol.* 175:2026–2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of Conditional Lethal Mutants by Transposon Mutagenesis

This technique, described by de Lorenzo, V. et al., *Gene* 123:17–24 (1993); Neuwald, A. F. et al., *Gene* 125: 69–73 (1993); and Takiff, H. E. et al., *J. Bacteriol.* 174:1544–1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of Conditional Lethal Mutants by Chemical Mutagenesis

This technique is described by Beckwith, J., *Methods in Enzymology* 204: 3–18(1991), the contents of which are incorporated herein by reference for background purposes. In this technique random chemical mutagenesis of target organism, growth at temperature other than physiological temperature (permissive temperature) and subsequent replica plating and growth at different temperature (e.g., 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antibacterials developed to cure established and chronic infections.

6) RT-PCR

Bacterial messenger RNA, preferably that of *Staphylococcus aureus*, is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of bacterial 16S ribosomal RNA, preferably that of *Staphylococcus aureus*, as detected by probing Northerns with a suitably labeled sequence specific oligonucleotide probe. Typically, a 5' dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI).

Use of the of these technologies when applied to the sequences of the invention enables ready identification of bacterial proteins expressed during infection, inhibitors of which would have utility in anti-bacterial therapy.

Deposited Materials

A deposit containing a *Staphylococcus aureus* WCUH 29 strain has been deposited with the National Collections of Industrial and Marine Bacteria Ltd. (NCIMB), 23 St. Machar Drive, Aberdeen AB2 1RY, Scotland on Sep. 11, 1995 and assigned NCIMB Deposit No. 40771. The *Staphylococcus aureus* strain deposit is referred to herein as "the deposited strain" or as "the DNA of the deposited strain."

The deposited material is a strain that contains the full length spoIIIE DNA, referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A license may be required to make, use or sell the deposited materials, and no such license is hereby granted.

Polypeptides

The polypeptides of the invention include the polypeptide of FIG. 2 [SEQ ID NO:2 AND SEQ ID NO:4] (in particular the mature polypeptide) as well as polypeptides and fragments, particularly those which have the biological activity of spoIIIE, and aslo those which have at least 70% identity to the polypeptide of FIG. 2 [SEQ ID NO:2 AND SEQ ID NO:4] or the relevant portion, preferably at least 80% identity to the polypeptide of FIG. 2 [SEQ ID NO:2 AND SEQ ID NO:4], and more preferably at least 90% similarity (more preferably at least 90% identity) to the polypeptide of FIG. 2 [SEQ ID NO:2 AND SEQ ID NO:4] and still more preferably at least 95% similarity (still more preferably at least 95% identity) to the polypeptide of FIG. 2 [SEQ ID NO:2 AND SEQ ID NO:4] and also include portions of such polypeptides with such portion of the polypeptide generally containing at least 30 amino acids and more preferably at least 50 amino acids.

Variants that are fragments of the polypeptides of the invention may be employed for producing the corresponding full-length polypeptide by peptide synthesis; therefore, these variants may be employed as intermediates for producing the full-length polypeptides. Variants that are fragments of the polynucleotides of the invention may be used to synthesize full-length polynucleotides of the invention.

A fragment is a variant polypeptide having an amino acid sequence that entirely is the same as part but not all of the amino acid sequence of the aforementioned polypeptides. As with spoIIIE polypeptides fragments may be "freestanding," or comprised within a larger polypeptide of which they form a part or region, most preferably as a single continuous region, a single larger polypeptide.

Preferred fragments include, for example, truncation polypeptides having a portion of the amino acid sequence of FIG. 2 [SEQ ID NO:2 AND SEQ ID NO:4], or of variants thereof, except for deletion of a continuous series of residues that includes the amino termninus, or a continuous series of residues that includes the carboxyl terminus or deletion of two continuous series of residues, one including the amino terminus and one including the carboxyl terminus. Degradation forms of the polypeptides of the invention in a host cell, particularly a *Staphylococcus aureus*, are also preferred. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of spoIIIE, including those with a similar activity or an improved activity, or with a decreased undesirable activity. Also included are those fragments that are antigenic or immunogenic in an animal, especially in a human.

Polynucleotides

Another aspect of the invention relates to isolated polynucleotides which encode the spoIIIE polypeptide having the deduced amino acid sequence of FIG. 2 [SEQ ID NO:2 AND SEQ ID NO:4] and polynucleotides closely related thereto and variants therto.

Using the information provided herein, such as the polynucleotide sequence set out in FIG. 1 [SEQ ID NO:1 AND SEQ ID NO:3], a polynucleotide of the invention encoding spoIIIE polypeptide may be obtained using standard cloning and screening, such as those for cloning and sequencing chromosomal DNA fragments from *Staphylococcus aureus* WCUH 29 cells as starting material, followed by obtaining a full length clone. For example, to obtain a polynucleotide sequence of the invention, such as that sequence given in FIG. 1 [SEQ ID NO:1 AND SEQ ID NO:3], typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70). Illustrative of the invention, the polynucleotide set out in FIG. 1 [SEQ ID NO:1 AND SEQ ID NO:3] was discovered in a DNA library derived from *Staphylococcus aureus* WCUH 29.

The DNA sequence thus obtained is set out in FIG. 1 [SEQ ID NO:1 AND SEQ ID NO:3]. It contains an open reading frame encoding a protein having about the number of amino acid residues set forth in FIG. 2 [SEQ ID NO:2 AND SEQ ID NO:4] with a deduced molecular weight that can be calculated using amino acid residue molecular weight values well known in the art. spoIIIE of the invention is structurally related to other proteins of the spo family, as shown by the results of sequencing the DNA encoding spoIIIE of the deposited strain. The protein exhibits greatest homology to *B. subtilis* spoIIIE protein among known proteins. spoIIIE of FIG. 2 [SEQ ID NO:2 AND SEQ ID NO:4] has about 49% identity over its entire length with the amino acid sequence of *B. subtilis* spoIIIE polypeptide.

Sequence of the invention may also be identical over its entire length to the coding sequence in FIG. 1 [SEQ ID NO:1 AND SEQ ID NO:3].

Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of this aspect of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767 (1984)). Polynucleotides of the invention also include, but are not limited to, polynucleotides comprising a structural gene and its naturally associated sequences that control gene expression.

In accordance with the foregoing, the term "polynucleotide encoding a polypeptide" as used herein encompasses polynucleotides which include a sequence encoding a polypeptide of the invention, particularly bacterial, and more particularly the *Staphylococcus aureus* spoIIIE having the amino acid sequence set out in FIG. 2 [SEQ ID NO:2 AND SEQ ID NO:4]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The invention further relates to variants of the herein above described polynucleotides which encode for variants of the polypeptide having the deduced amino acid sequence of FIG. 2 [SEQ ID NO:2 AND SEQ ID NO:4].

Further particularly preferred embodiments are polynucleotides encoding spoIIIE variants, which have the amino acid sequence of spoIIIE polypeptide of FIG. 2 [SEQ ID NO:2 AND SEQ ID NO:4] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of spoIIIE.

Further preferred embodiments of the invention are polynucleotides that are at least 50%, 60% or 70% identical over their entire length to a polynucleotide encoding spoIIIE polypeptide having the amino acid sequence set out in FIG. 2 [SEQ ID NO:2 AND SEQ ID NO:4], and polynucleotides which are complementary to such polynucleotides. Alternatively, most highly preferred are polynucleotides that comprise a region that is at least 80% identical over their entire length to a polynucleotide encoding spoIIIE polypeptide of the *Staphylococcus aureus* DNA of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments in this respect, moreover, are polynucleotides which encode polypeptides which retain substantially the same biological function or activity as the mature polypeptide encoded by the DNA of FIG. 1 [SEQ ID NO:1 AND SEQ ID NO:3].

The invention further relates to polynucleotides that hybridize to the herein above-described sequences. In this regard, the invention especially relates to polynucleotides which hybridize under stringent conditions to the herein above-described polynucleotides. As herein used, the terms "stringent conditions" and a "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

The invention also provides a polynucleotide consisting essentially of a polynucleotide sequence obtainable by screening an appropriate library containing the complete gene for a polynucleotide sequence set forth in SEQ ID NO:1 AND SEQ ID NO:3 under stringent hybridization conditions with a probe having the sequence of said polynucleotide sequence set forth in SEQ ID NO:1 AND SEQ ID NO:3 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding spoIIIE and to isolate cDNA and genomic clones of other genes that have a high sequence similarity to the spoIIIE gene. Such probes generally will comprise at least 15 bases. Preferably, such probes will have at least 30 bases and may have at least 50 bases. Particularly preferred probes will have at least 30 bases and will have 50 bases or less.

For example, the coding region of the spoIIIE gene may be isolated by screening using the known DNA sequence to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed as research reagents and materials for discovery of treatments of and diagnostics for disease, particularly human disease, as further discussed herein relating to polynucleotide assays, inter alia.

Polynucleotides of the invention that are oligonucleotides derived from the sequences of SEQ ID NOS:1 and 2 may be used in the processes herein as described, but preferably for PCR, to determine whether or not the polynucleotides identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors which comprise a polynucleotide or polynucleotides of the invention, host cells which are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the spoIIIE polynucleotides of the invention for use as diagnostic reagents. Detection of spoIIIE in a eukaryote, particularly a mammal, and especially a human, will provide a diagnostic method for diagnosis of a disease. Eukaryotes (herein also "individual(s)"), particularly mammals, and especially humans, infected with an organism comprising the spoIIIE gene may be detected at the DNA level by a variety of techniques.

Nucleic acids for diagnosis may be obtained from an infected individual's cells and tissues, such as bone, blood, muscle, cartilage, and skin. Genomnic DNA may be used directly for detection or may be amplified enzymatically by using PCR or other amplification technique prior to analysis. RNA or cDNA may also be used in the same ways. Using amplification, characterization of the strain of prokaryote present in a eukaryote, particularly a mammal, and especially a human, may be made by an analysis of the genotype of the prokaryote gene. Deletions and insertions can be detected by a change in size of the amplified product in comparison to the genotype of a reference sequence. Point mutations can be identified by hybridizing amplified DNA to labeled spoIIIE polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science,* 230: 1242 (1985). Sequence changes at specific locations also may be revealed by nuclease protection assays, such as RNase and S1 protection or a chemical cleavage method. See, e.g., Cotton et al., *Proc. Natl. Acad. Sci, USA,* 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding SpoIIIE can be used to identify and analyze mutations These primers may be used for amplifying spoIIIE DNA isolated from a sample derived from an individual. The invention also provides these primers with 1, 2, 3 or 4 nucleotides removed from the 5' and/or the 3' end. The primers may be used to amplify the gene isolated from an infected individual such that the gene may then be subject to various techniques for elucidation of the DNA sequence. In this way, mutations in the DNA sequence may be detected and used to diagnose infection and to serotype or classify the infectious agent.

The invention provides a process for diagnosing, disease, preferably bacterial infections, more preferably infections by *Staphylococcus aureus*, and most preferably disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis), comprising determining from a sample derived from an individual a increased level of expression of polynucleotide having the sequence of FIG. 1 [SEQ ID NO: 1]. Increased or decreased expression of spoIIIE polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of spoIIIE protein compared to normal control tissue samples may be used to detect the presence of an infection, for example. Assay techniques that can be used to determine levels of a spoIIIE protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art which provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against spoIIIE may be employed to treat infections, particularly bacterial infections and especially disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Polypeptide variants include antigenically, epitopically or immunologically equivalent variants which form a particular aspect of this invention. The term "antigenically equivalent derivative" as used herein encompasses a polypeptide or its equivalent which will be specifically recognised by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Antagonists and Agonists—Assays and Molecules

The invention also provides a method of screening compounds to identify those which enhance (agonist) or block (antagonist) the action of spoIIIE polypeptides or polynucleotides.

For example, to screen for agonists or antagoists, a synthetic reaction mix, a cellular compartment, such as a membrane, cell envelope or cell wall, or a preparation of any thereof, comprising spoIIIE polypeptide and a labeled substrate of such polypeptide is incubated in the absence or the presence of a candidate molecule which may be a spoIIIE agonist or antagonist. The ability of the candidate molecule to agonize or antagonize the spoIIIE polypeptide is reflected in decreased binding of the labeled ligand or decreased production of product from such substrate. Molecules which bind gratuitously, i.e., without inducing the effects of spoIIIE are most likely to be good antagonists. Molecules that bind well and increase the rate of product production from substrate are agonists. The rate or level of production of product from substrate may be enhanced by using a reporter system. Reporter systems that may be useful in this regard include but are not limited to colorimetric labeled substrate converted into product, a reporter gene that is responsive to changes in spoIIIE activity, and binding assays known in the art.

Another example of an assay for SpoIIIE antagonists is a competitive assay that combines spoIIIE and a potential antagonist with spoIIIE-binding molecules, recombinant spoIIIE binding molecules, natural substrates or ligands, or substrate or ligand mimetics, under appropriate conditions for a competitive inhibition assay. spoIIIE can be labeled, such as by radioactivity or a colorimetric compound, such that the number of spoIIIE molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing spoIIIE-induced activities, thereby preventing the action of spoIIIE by excluding spoIIIE from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of spoIIIE.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block spoIIIE protein mediated mammalian cell invasion by, for example, initiating phosphorylation of mammalian tyrosine kinases (Rosenshine et al., *Infect. Immun.* 60:2211 (1992); iii) to block bacterial adhesion between mammalian extracellular matrix proteins and bacterial spoIIIE proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

This invention provides a method of screening drugs to identify those which interfere with the mechanism of action of the SpoIIIE protein such that it is inhibited, the method comprising contacting the. SpoIIIE protein with the drug and measuring the inhibition of SpoIIIE activity. The polypeptide in any of the forms described above, purified using any of the methods described above, can be used to configure an in vitro assay based on its mechanism of action, for example in the presence of purified bacterial membranes or vesicles or synthetic phospholipid membrane mimics or in the appropriate enzyme buffer if membranes are not required and including the incorporation of additional macromolecular or low molecular weight cofactors which are either necessary for, or potentate, the activities of SpoIIIE protein.

Examples of assays relating to the invention are set forth below:

(1) Nucleoside 5'-triphosphate Binding and 5'-triphosphatase Activity. The binding of nucleoside 5'-triphosphates (NTPs), such as adenosine 5'-triphosphate (ATP) to, and the subsequent hydrolysis by, SpoIIIE protein provides for two potential in vitro assay formats. Nucleotide binding assays may be based on homogeneous or heterogeneous measurements and using radioactively labelled nucleotide (photoaffinity cross linking, gel filtration, filter binding) and using a molecular optical signal to report upon, and monitor the extent of, the binding of nucleotide or of a fluorescent/chromophoric nucleotide derivative (fluorescence intensity, anisotropy, fluctuation correlation and energy transfer measurements, absorbance and circular dichroism measurements). The ability of SpoIIIE protein, either in the presence or absence of additional cofactors, to catalyse nucleotide hydrolysis is monitored by the change in substrate (NTP) and/or product (NDP, inorganic phosphate) concentration using either direct (radioactivity, colorimetric) or coupled enzyme formats.

(2) Nucleic Acid Binding and Vectorial Translocation Activity. The interaction of SpoIIIE protein with either natural or synthetic oligonucleotide or polynucleotide ribonucleic acids (RNA) or deoxyribonucleic acids (DNA), or analogues thereof, can be assayed using materials and methods analogous to those described in (1) above for the binding of nucleoside triphosphates and which are obvious to a practitioner skilled in the art of protein biochemistry and nucleic acid molecular biology. The DNA binding site sequence may be identified by making random pools of oligonucleotides and identifying the sequence of the ones which bind iteratively, or by recovery, amplification and sequencing of the DNA. Furthermore, the vectorial motion of nucleic acids due to the action of SpoIIIE through a well defined physical boundary (e.g a lipid vesicle, biological membrane), either in the presence or absence of additional macromolecular and low molecular weight cofactors, can be measured using either a solution based or heterogeneous separation format linked to an optical or radioactive measurement. For example, an assay could use vesicles with a pH gradient across the boundary and a fluorescein-labelled nucleic acid. The translocation of the nucleic acid into the vesicle due to the action of SpoIIIE would result in a measurable quenching of the fluorescein fluorescence.

(3) Protein:Protein Interactions: The measurement of the interaction of SpoIIIE protein with additional proteins or peptides, either within a lipid-based membrane system or in solution, provides for a potential assay format. Heterogeneous assays encompassing the use of an immunoassay or surface-coating format in conjunction with either radiolabelled or optically labelled proteins and components are envisaged. The interaction of unlabelled SpoIIIE with other polypeptides can also be observed directly using surface plasmon resonance technology in optical biosensor devices. This method is particularly useful for measuring interactions with larger (>5 kDa) polypeptides and can be adapted to screen for inhibitors of the protein-protein interaction. Solution-based homogeneous assays using fluorescently-labelled components may be configured to report on changes in fluorescence intensity, fluorescence anisotropy, fluorescence energy transfer or correlation fluctuations in intensity as a result of the binding interaction. Binding proteins useful in these types of assay may be identified by 'ligand fishing' using, for example, optical biosensor methods and bacterial extracts followed by affinity capture or chromatography on immobilised SpoIIIE. Optionally, derivatives of SpoIIIE with aminoacid sequences altered to improve aqueous solubility may be employed. Solution-phase capture of SpoIIIE binding proteins may be carried out by mixing soluble SpoIIIE with, for example, a detergent extract and reisolating a complex by use of anti-SpoIIIE antibodies or by tagging the SpoIIIE with, for example, Biotin and capture on immobilised avidin or streptavidin. Following elution of binding proteins from immobilised SpoIIIE using salt, pH changes or chaotropic agents, the eluted protein products may be separated using high-resolution methods such as reverse-phase high performance liquid chromatography and the individual polypeptides characterised by N-terminal aminoacid sequencing and/or mass mapping (mass spectrometry combined with molecular ion weight matching against a protein database.

(4) Microsocopy: pure SpoIIIE protein is used to raise antibodies in mice or rabbits or other suitable animal host, which antibodies are conjugated to gold particles attached to a secondary antibody. Actively dividing cells are sampled, the gold conjugate is added, and the sample prepared for electon microscopy using standard techniques and visualise to see the localisation of the protein and any effect of test drug.

The antagonists and agonists may be employed for instance to inhibit disease, such as, infections of the upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis) bone and joint (e.g. septic arthritis, osteomyelitis).

Vaccines

Another aspect of the invention relates to a method for inducing an immunological response in an individual, particularly a mammal which comprises inoculating the individual with spoIIIE, or a fragment or variant thereof, adequate to produce antibody to protect said individual from infection, particularly bacterial infection and most particularly Staphylococcus aureus infections. Yet another aspect of the invention relates to a method of inducing immunological response in an individual which comprises, through gene therapy, delivering gene encoding spoIIIE, or a fragment or a variant thereof, for expressing spoIIIE, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a spoIIIE or protein coded therefrom, wherein the composition comprises a recombinant spoIIIE or protein coded therefrom comprising DNA which codes for and expresses an antigen of said spoIIIE or protein coded therefrom.

The spoIIIE or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with Staphylococcus aureus will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly Staphylococcus aureus infections, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain spoIIIE, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or the agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially Staphylococcus aureus wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10mg/ml for bathing of wounds or indwelling devices.

A vaccine composition is conveniently in injectable form. Conventional adjuvants may be employed to enhance the immune response. A suitable unit dose for vaccination is 0.5–5 μg/kg of antigen, and such dose is preferably administered 1–3 times and with an interval of 1–3 weeks. With the indicated dose range, no adverse toxicological effects will be observed with the compounds of the invention which would preclude their administration to suitable individuals.

The antibodies described above may also be used as diagnostic reagents to detect the presence of bacteria containing the spoIIIE protein.

EXAMPLES

The examples below are carried out using standard techniques, which are well known and routine to those of skill in the art, except where otherwise described in detail. The examples are illustrative, but do not limit the invention.

Example 1

Isolation of DNA Coding for a Novel SpoIIIE Protein from S. aureus WCUH 29

The polynucleotide having the DNA sequence given in SEQ ID NO:1 was obtained from a library of clones of chromosomal DNA of S.aureus WCUH 29 in E.coli. Libraries may be prepared by routine methods, for example:

Methods 1 and 2

Total cellular DNA is isolated from Staphylococcus aureus strain WCUH29 (NCIMB 40771) according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E.coli infected with the packaged library. The library is amplified by standard procedures.

Method 2

Total cellular DNA is partially hydrolysed with a combination of four restriction enzymes (RsaI, PalI, AluI and Bsh1235I) and size-fractionated according to standard procedures. EcoRI linkers are ligated to the DNA and the fragments then ligated into the vector Lambda ZapII that have been cut with EcoRI, the library packaged by standard procedures, and E.coli infected with the packaged library. The library is amplified by standard procedures.

What is claimed is:

1. An isolated protein comprising a polypeptide comprising the amino acid sequence set forth in SEQ ID NO:2.

2. A composition comprising the isolated protein of claim 1 and a pharmaceutically acceptable carrier.

3. An isolated fusion protein comprising a heterologous amino acid sequence fused to the polypeptide of claim 2.

4. A composition comprising the isolated fusion protein of claim 3 and a pharmaceutically acceptable carrier.

5. The isolated protein of claim 1, wherein the isolated protein consists of the amino acid sequence set forth in SEQ ID NO:2.

6. A composition comprising the isolated protein of claim 5 and a pharmaceutically acceptable carrier.

7. An isolated protein comprising a polypeptide comprising the amino acid sequence set forth in SEQ ID NO:4.

8. A composition comprising the isolated protein of claim 7 and a pharmaceutically acceptable carrier.

9. An isolated fusion protein comprising a heterologous amino acid sequence fused to the polypeptide of claim 7.

10. A composition comprising the isolated fusion protein of claim 9 and a pharmaceutically acceptable carrier.

11. The isolated protein of claim 7, wherein the isolated protein consists of the amino acid sequence set forth in SEQ ID NO:4.

12. A composition comprising the isolated protein of claim 11 and a pharmaceutically acceptable carrier.

* * * * *

SEQUENCE LISTING

<160> NUMBER OF SEQ ID NOS: 4

<210> SEQ ID NO 1
<211> LENGTH: 2367
<212> TYPE: DNA
<213> ORGANISM: Staphylococcus aureus

<400> SEQUENCE: 1

```
ttggctcaag caaaaaagaa atcgacagct aagaaaaaaa cagcatcaaa aaaaagaaca      60
aattcaagga aaagaagaa tgataatccg atacgttatg tcatagctat tttagtagtt     120
gtattaatgg tgttgggtgt tttccaatta ggaataatcg gtcgtctaat tgacagcttc     180
tttaattatt tatttgggta cagtagatat ttaacatata ttttagtact cttagcaact     240
ggttttatta catactctaa acgtattcct aaaactagac gaacggctgg ttcgattgta     300
ttgcaaattg cattgctatt tgtatcacag ttagttttc attttaatag tggtatcaaa      360
gctgaaagag aacctgtact ttcttatgta tatcagtcat accaacacag tcattttcca     420
aattttggtg gcggtgtatt aggttttat ttattagagt taagcgtacc tttaatttca      480
ttatttggtg tatgtattat tactatttta ttattatgct caagtgttat tttattaaca     540
aaccatcaac atcgtgatgt tgcaaaagtt gcactggaaa atataaaagc ttggtttggt     600
tcatttaatg aaaaaatgtc ggaaagaaac caagaaaaac aattgaagcg tgaagaaaaa     660
gcgagactta aagaagaaca aaaggcacgt caaaatgaac agccacaaat aaaagatgtg     720
agtgatttta cggaagtgcc tcaagaaaga gatattccaa tttatgggca tactgaaaat     780
gaaagtaaaa gccagtgtca accagtcga aaaaaacgag tgtttgatgc agagaatagt      840
tcgaataaca tcgtaaatca tcaagcagat cagcaagagc aattaacaga acaaactcat     900
aacagtgttg aaagtgaaaa cactattgaa gaagctggtg aagttacgaa tgtatcgtat     960
gttgttccac cgttaacttt acttaatcaa cctgcaaaac aaaaagcaac atctaaagct    1020
gaagtacaac gtaaaggaca agtactagag aatacattaa aagattttgg ggtaaatgca    1080
aaagtgacac aaattaaaat tggtcctgca gtaactcaat atgaaattca accagctcaa    1140
gggggttaaag tgagtaaat tgtaaacttg cataatgata ttgcattagc tttagcagca    1200
aaagatgtta gaatcgaagc accaatacct ggtcgctctg cagtaggtat tgaagtgcca    1260
aatgagaaaa tttcattagt ttcactaaaa gaagttttag atgaaaaatt cccgtctaat    1320
aataaactag aagttggatt aggaagagat atatcaggtg atccaattac tgttccacta    1380
aatgaaatgc cacacttatt ggtggcagga tcgacgggta gtggtaaatc tgttttgtata    1440
aatggtatta ttacaagtat tttattaaat gctaagccgc atgaagttaa acttatgtta    1500
atcgatccga aaatggttga actaaatgtt tataacggaa ttccacattt attaattccg    1560
gttgttacaa atcctcataa agctgctcaa gctttagaaa aaattgtagc tgagatggaa    1620
agacgttatg atttattcca acattcatca actagaaata ttaaaggtta taacgaatta    1680
atccgtaagc aaaatcaaga attagatgag aagcaaccag aattaccta tatcgttgtt    1740
attgtagatg agcttgcaga tttaatgatg gtagctggta agaagttga aaatgcgatt    1800
caacgtatca cacaaatggc acgtgcagca ggtatacatt tgattgtagc aacacaaaga    1860
ccttctgtgg atgtaattac aggtatcatt aaaaataaca ttccatctag aattgctttt    1920
gctgtgagtt ctcaaacaga ttcaagaact attattggta ctggcggcgc agaaaagtta    1980
cttggtaaag gtgacatgtt atacgttgga atggtgatt catcacaaac acgtattcaa    2040
ggggcgtttt taagtgacca agaggtgcaa gatgttgtaa attatgtagt agaacaacaa    2100
caggcaaatt atgtaaaaga atggaacca gatgcaccag tggataaatc ggaaatgaaa    2160
agtgaagatg ctttatatga tgaagcgtat ttgtttgttg ttgaacaaca aaaggcaagt    2220
acatcattgt tacaacgcca atttagaatt ggttataata gagcatctag gttgatggat    2280
```

-continued

```
gatttagaac gcaatcaggt aatcggtcca caaaaaggaa gcaagcctag acaagtttta    2340
atagatctta ataatgacga ggtgtaa                                         2367
```

<210> SEQ ID NO 2
<211> LENGTH: 788
<212> TYPE: PRT
<213> ORGANISM: Staphylococcus aureus

<400> SEQUENCE: 2

```
Leu Ala Gln Ala Lys Lys Ser Thr Ala Lys Lys Thr Ala Ser
  1               5                  10                  15

Lys Lys Arg Thr Asn Ser Arg Lys Lys Asn Asp Asn Pro Ile Arg
             20                  25                  30

Tyr Val Ile Ala Ile Leu Val Val Leu Met Val Leu Gly Val Phe
             35                  40                  45

Gln Leu Gly Ile Ile Gly Arg Leu Ile Asp Ser Phe Phe Asn Tyr Leu
 50                              55                  60

Phe Gly Tyr Ser Arg Tyr Leu Thr Tyr Ile Leu Val Leu Leu Ala Thr
 65                  70                  75                  80

Gly Phe Ile Thr Tyr Ser Lys Arg Ile Pro Lys Thr Arg Thr Ala
                 85                  90                  95

Gly Ser Ile Val Leu Gln Ile Ala Leu Leu Phe Val Ser Gln Leu Val
                100                 105                 110

Phe His Phe Asn Ser Gly Ile Lys Ala Glu Arg Glu Pro Val Leu Ser
                115                 120                 125

Tyr Val Tyr Gln Ser Tyr Gln His Ser His Phe Pro Asn Phe Gly Gly
                130                 135                 140

Gly Val Leu Gly Phe Tyr Leu Leu Glu Leu Ser Val Pro Leu Ile Ser
145                 150                 155                 160

Leu Phe Gly Val Cys Ile Ile Thr Ile Leu Leu Cys Ser Ser Val
                165                 170                 175

Ile Leu Leu Thr Asn His Gln His Arg Asp Val Ala Lys Val Ala Leu
                180                 185                 190

Glu Asn Ile Lys Ala Trp Phe Gly Ser Phe Asn Glu Lys Met Ser Glu
                195                 200                 205

Arg Asn Gln Glu Lys Gln Leu Lys Arg Glu Glu Lys Ala Arg Leu Lys
                210                 215                 220

Glu Glu Gln Lys Ala Arg Gln Asn Glu Gln Pro Gln Ile Lys Asp Val
225                 230                 235                 240

Ser Asp Phe Thr Glu Val Pro Gln Glu Arg Asp Ile Pro Ile Tyr Gly
                245                 250                 255

His Thr Glu Asn Glu Ser Lys Ser Gln Cys Gln Pro Ser Arg Lys Lys
                260                 265                 270

Arg Val Phe Asp Ala Glu Asn Ser Ser Asn Asn Ile Val Asn His Gln
                275                 280                 285

Ala Asp Gln Gln Glu Gln Leu Thr Glu Gln Thr His Asn Ser Val Glu
                290                 295                 300

Ser Glu Asn Thr Ile Glu Glu Ala Gly Glu Val Thr Asn Val Ser Tyr
305                 310                 315                 320

Val Val Pro Pro Leu Thr Leu Leu Asn Gln Pro Ala Lys Gln Lys Ala
                325                 330                 335

Thr Ser Lys Ala Glu Val Gln Arg Lys Gly Gln Val Leu Glu Asn Thr
                340                 345                 350
```

```
Leu Lys Asp Phe Gly Val Asn Ala Lys Val Thr Gln Ile Lys Ile Gly
        355                 360                 365

Pro Ala Val Thr Gln Tyr Glu Ile Gln Pro Ala Gln Gly Val Lys Val
        370                 375                 380

Ser Lys Ile Val Asn Leu His Asn Asp Ile Ala Leu Ala Leu Ala Ala
385                 390                 395                 400

Lys Asp Val Arg Ile Glu Ala Pro Ile Pro Gly Arg Ser Ala Val Gly
                405                 410                 415

Ile Glu Val Pro Asn Glu Lys Ile Ser Leu Val Ser Leu Lys Glu Val
                420                 425                 430

Leu Asp Glu Lys Phe Pro Ser Asn Asn Lys Leu Glu Val Gly Leu Gly
        435                 440                 445

Arg Asp Ile Ser Gly Asp Pro Ile Thr Val Pro Leu Asn Glu Met Pro
        450                 455                 460

His Leu Leu Val Ala Gly Ser Thr Gly Ser Gly Lys Ser Val Cys Ile
465                 470                 475                 480

Asn Gly Ile Ile Thr Ser Ile Leu Leu Asn Ala Lys Pro His Glu Val
                485                 490                 495

Lys Leu Met Leu Ile Asp Pro Lys Met Val Glu Leu Asn Val Tyr Asn
                500                 505                 510

Gly Ile Pro His Leu Leu Ile Pro Val Val Thr Asn Pro His Lys Ala
        515                 520                 525

Ala Gln Ala Leu Glu Lys Ile Val Ala Glu Met Glu Arg Arg Tyr Asp
530                 535                 540

Leu Phe Gln His Ser Ser Thr Arg Asn Ile Lys Gly Tyr Asn Glu Leu
545                 550                 555                 560

Ile Arg Lys Gln Asn Gln Glu Leu Asp Glu Lys Gln Pro Glu Leu Pro
                565                 570                 575

Tyr Ile Val Val Ile Val Asp Glu Leu Ala Asp Leu Met Met Val Ala
                580                 585                 590

Gly Lys Glu Val Glu Asn Ala Ile Gln Arg Ile Thr Gln Met Ala Arg
        595                 600                 605

Ala Ala Gly Ile His Leu Ile Val Ala Thr Gln Arg Pro Ser Val Asp
        610                 615                 620

Val Ile Thr Gly Ile Ile Lys Asn Asn Ile Pro Ser Arg Ile Ala Phe
625                 630                 635                 640

Ala Val Ser Ser Gln Thr Asp Ser Arg Thr Ile Ile Gly Thr Gly Gly
                645                 650                 655

Ala Glu Lys Leu Leu Gly Lys Gly Asp Met Leu Tyr Val Gly Asn Gly
                660                 665                 670

Asp Ser Ser Gln Thr Arg Ile Gln Gly Ala Phe Leu Ser Asp Gln Glu
        675                 680                 685

Val Gln Asp Val Val Asn Tyr Val Val Glu Gln Gln Ala Asn Tyr
        690                 695                 700

Val Lys Glu Met Glu Pro Asp Ala Pro Val Asp Lys Ser Glu Met Lys
705                 710                 715                 720

Ser Glu Asp Ala Leu Tyr Asp Glu Ala Tyr Leu Phe Val Val Glu Gln
                725                 730                 735

Gln Lys Ala Ser Thr Ser Leu Leu Gln Arg Gln Phe Arg Ile Gly Tyr
        740                 745                 750

Asn Arg Ala Ser Arg Leu Met Asp Asp Leu Glu Arg Asn Gln Val Ile
        755                 760                 765
```

Gly Pro Gln Lys Gly Ser Lys Pro Arg Gln Val Leu Ile Asp Leu Asn
    770             775                 780

Asn Asp Glu Val
785

<210> SEQ ID NO 3
<211> LENGTH: 2241
<212> TYPE: DNA
<213> ORGANISM: Staphylococcus aureus

<400> SEQUENCE: 3

| | | | | | |
|---|---|---|---|---|---|
| atggtgttgg | gtgttttcca | attaggaata | atcggtcgtc | taattgacag | cttcttaat | 60 |
| tatttatttg | ggtacagtag | atatttaaca | tatattttag | tactcttagc | aactggtttt | 120 |
| attacatact | ctaaacgtat | tcctaaaact | agacgaacgg | ctggttcgat | tgtattgcaa | 180 |
| attgcattgc | tatttgtatc | acagttagtt | tttcatttta | atagtggtat | caaagctgaa | 240 |
| agagaacctg | tactttctta | tgtatatcag | tcataccaac | acagtcattt | tccaaatttt | 300 |
| ggtggcggtg | tattaggttt | ttatttatta | gagttaagcg | tacctttaat | ttcattattt | 360 |
| ggtgtatgta | ttattactat | tttattatta | tgctcaagtg | ttattttatt | aacaaaccat | 420 |
| caacatcgtg | atgttgcaaa | agttgcactg | gaaaatataa | aagcttggtt | tggttcattt | 480 |
| aatgaaaaaa | tgtcggaaag | aaaccaagaa | aaacaattga | agcgtgaaga | aaaagcgaga | 540 |
| cttaaagaag | aacaaaaggc | acgtcaaaat | gaacagccac | aaataaaaga | tgtgagtgat | 600 |
| tttacggaag | tgcctcaaga | aagagatatt | ccaatttatg | ggcatactga | aaatgaaagt | 660 |
| aaaagccagt | gtcaaccaag | tcgaaaaaaa | cgagtgtttg | atgcagagaa | tagttcgaat | 720 |
| aacatcgtaa | atcatcaagc | agatcagcaa | gagcaattaa | cagaacaaac | tcataacagt | 780 |
| gttgaaagtg | aaaacactat | tgaagaagct | ggtgaagtta | cgaatgtatc | gtatgttgtt | 840 |
| ccaccgttaa | ctttacttaa | tcaacctgca | aaacaaaaag | caacatctaa | agctgaagta | 900 |
| caacgtaaag | gacaagtact | agagaataca | ttaaaagatt | ttggggtaaa | tgcaaaagtg | 960 |
| acacaaatta | aaattggtcc | tgcagtaact | caatatgaaa | ttcaaccagc | tcaaggggtt | 1020 |
| aaagtgagta | aaattgtaaa | cttgcataat | gatattgcat | tagctttagc | agcaaaagat | 1080 |
| gttagaatcg | aagcaccaat | acctggtcgc | tctgcagtag | gtattgaagt | gccaaatgag | 1140 |
| aaaatttcat | tagtttcact | aaaagaagtt | ttagatgaaa | aattcccgtc | taataataaa | 1200 |
| ctagaagttg | gattaggaag | agatatatca | ggtgatccaa | ttactgttcc | actaaatgaa | 1260 |
| atgccacact | tattggtggc | aggatcgacg | ggtagtggta | atctgtttg | tataaatggt | 1320 |
| attattacaa | gtattttatt | aaatgctaag | ccgcatgaag | ttaaacttat | gttaatcgat | 1380 |
| ccgaaaatgg | ttgaactaaa | tgttatatac | ggaattccac | atttattaat | tccggttgtt | 1440 |
| acaaatcctc | ataaagctgc | tcaagcttta | gaaaaaattg | tagctgagat | ggaaagacgt | 1500 |
| tatgatttat | tccaacattc | atcaactaga | aatattaaag | gttataacga | attaatccgt | 1560 |
| aagcaaaatc | aagaattaga | tgagaagcaa | ccagaattac | cttatatcgt | tgttattgta | 1620 |
| gatgagcttg | cagatttaat | gatggtagct | ggtaaagaag | ttgaaaatgc | gattcaacgt | 1680 |
| atcacacaaa | tggcacgtgc | agcaggtata | catttgattg | tagcaacaca | agaccttct | 1740 |
| gtggatgtaa | ttacaggtat | cattaaaaat | aacattccat | ctagaattgc | ttttgctgtg | 1800 |
| agttctcaaa | cagattcaag | aactattatt | ggtactggcg | gcgcagaaaa | gttacttggt | 1860 |
| aaaggtgaca | tgttatacgt | tggaaatggt | gattcatcac | aaacacgtat | tcaagggcg | 1920 |
| tttttaagtg | accaagaggt | gcaagatgtt | gtaaattatg | tagtagaaca | acaacaggca | 1980 |

-continued

```
aattatgtaa aagaaatgga accagatgca ccagtggata atcggaaat gaaagtgaa    2040 gatgctttat atgatgaagc gtatttgttt gttgttgaac aacaaaaggc aagtacatca    2100
ttgttacaac gccaatttag aattggttat aatagagcat ctaggttgat ggatgattta    2160
gaacgcaatc aggtaatcgg tccacaaaaa ggaagcaagc ctagacaagt tttaatagat    2220
cttaataatg acgaggtgta a                                             2241
```

<210> SEQ ID NO 4
<211> LENGTH: 746
<212> TYPE: PRT
<213> ORGANISM: Staphylococcus aureus

<400> SEQUENCE: 4

```
Met Val Leu Gly Val Phe Gln Leu Gly Ile Ile Gly Arg Leu Ile Asp
 1               5                  10                  15

Ser Phe Phe Asn Tyr Leu Phe Gly Tyr Ser Arg Tyr Leu Thr Tyr Ile
                20                  25                  30

Leu Val Leu Leu Ala Thr Gly Phe Ile Thr Tyr Ser Lys Arg Ile Pro
            35                  40                  45

Lys Thr Arg Arg Thr Ala Gly Ser Ile Val Leu Gln Ile Ala Leu Leu
        50                  55                  60

Phe Val Ser Gln Leu Val Phe His Phe Asn Ser Gly Ile Lys Ala Glu
65                  70                  75                  80

Arg Glu Pro Val Leu Ser Tyr Val Tyr Gln Ser Tyr Gln His Ser His
                85                  90                  95

Phe Pro Asn Phe Gly Gly Val Leu Gly Phe Tyr Leu Leu Glu Leu
                100                 105                 110

Ser Val Pro Leu Ile Ser Leu Phe Gly Val Cys Ile Ile Thr Ile Leu
            115                 120                 125

Leu Leu Cys Ser Ser Val Ile Leu Leu Thr Asn His Gln His Arg Asp
        130                 135                 140

Val Ala Lys Val Ala Leu Glu Asn Ile Lys Ala Trp Phe Gly Ser Phe
145                 150                 155                 160

Asn Glu Lys Met Ser Glu Arg Asn Gln Glu Lys Gln Leu Lys Arg Glu
                165                 170                 175

Glu Lys Ala Arg Leu Lys Glu Glu Gln Lys Ala Arg Gln Asn Glu Gln
            180                 185                 190

Pro Gln Ile Lys Asp Val Ser Asp Phe Thr Glu Val Pro Gln Glu Arg
        195                 200                 205

Asp Ile Pro Ile Tyr Gly His Thr Glu Asn Glu Ser Lys Ser Gln Cys
    210                 215                 220

Gln Pro Ser Arg Lys Lys Arg Val Phe Asp Ala Glu Asn Ser Asn
225                 230                 235                 240

Asn Ile Val Asn His Gln Ala Asp Gln Gln Glu Gln Leu Thr Glu Gln
                245                 250                 255

Thr His Asn Ser Val Glu Ser Glu Asn Thr Ile Glu Glu Ala Gly Glu
            260                 265                 270

Val Thr Asn Val Ser Tyr Val Val Pro Pro Leu Thr Leu Leu Asn Gln
        275                 280                 285

Pro Ala Lys Gln Lys Ala Thr Ser Lys Ala Glu Val Gln Arg Lys Gly
    290                 295                 300

Gln Val Leu Glu Asn Thr Leu Lys Asp Phe Gly Val Asn Ala Lys Val
305                 310                 315                 320
```

-continued

```
Thr Gln Ile Lys Ile Gly Pro Ala Val Thr Gln Tyr Glu Ile Gln Pro
            325                 330                 335

Ala Gln Gly Val Lys Val Ser Lys Ile Val Asn Leu His Asn Asp Ile
            340                 345                 350

Ala Leu Ala Leu Ala Ala Lys Asp Val Arg Ile Glu Ala Pro Ile Pro
            355                 360                 365

Gly Arg Ser Ala Val Gly Ile Glu Val Pro Asn Glu Lys Ile Ser Leu
    370                 375                 380

Val Ser Leu Lys Glu Val Leu Asp Glu Lys Phe Pro Ser Asn Asn Lys
385                 390                 395                 400

Leu Glu Val Gly Leu Gly Arg Asp Ile Ser Gly Asp Pro Ile Thr Val
            405                 410                 415

Pro Leu Asn Glu Met Pro His Leu Leu Val Ala Gly Ser Thr Gly Ser
            420                 425                 430

Gly Lys Ser Val Cys Ile Asn Gly Ile Ile Thr Ser Ile Leu Leu Asn
    435                 440                 445

Ala Lys Pro His Glu Val Lys Leu Met Leu Ile Asp Pro Lys Met Val
    450                 455                 460

Glu Leu Asn Val Tyr Asn Gly Ile Pro His Leu Leu Ile Pro Val Val
465                 470                 475                 480

Thr Asn Pro His Lys Ala Ala Gln Ala Leu Glu Lys Ile Val Ala Glu
            485                 490                 495

Met Glu Arg Arg Tyr Asp Leu Phe Gln His Ser Ser Thr Arg Asn Ile
            500                 505                 510

Lys Gly Tyr Asn Glu Leu Ile Arg Lys Gln Asn Gln Glu Leu Asp Glu
    515                 520                 525

Lys Gln Pro Glu Leu Pro Tyr Ile Val Ile Val Asp Glu Leu Ala
    530                 535                 540

Asp Leu Met Met Val Ala Gly Lys Glu Val Glu Asn Ala Ile Gln Arg
545                 550                 555                 560

Ile Thr Gln Met Ala Arg Ala Ala Gly Ile His Leu Ile Val Ala Thr
            565                 570                 575

Gln Arg Pro Ser Val Asp Val Ile Thr Gly Ile Ile Lys Asn Asn Ile
            580                 585                 590

Pro Ser Arg Ile Ala Phe Ala Val Ser Ser Gln Thr Asp Ser Arg Thr
    595                 600                 605

Ile Ile Gly Thr Gly Gly Ala Glu Lys Leu Leu Gly Lys Gly Asp Met
    610                 615                 620

Leu Tyr Val Gly Asn Gly Asp Ser Ser Gln Thr Arg Ile Gln Gly Ala
625                 630                 635                 640

Phe Leu Ser Asp Gln Glu Val Gln Asp Val Val Asn Tyr Val Val Glu
            645                 650                 655

Gln Gln Gln Ala Asn Tyr Val Lys Glu Met Glu Pro Asp Ala Pro Val
            660                 665                 670

Asp Lys Ser Glu Met Lys Ser Glu Asp Ala Leu Tyr Asp Glu Ala Tyr
    675                 680                 685

Leu Phe Val Val Glu Gln Gln Lys Ala Ser Thr Ser Leu Leu Gln Arg
    690                 695                 700

Gln Phe Arg Ile Gly Tyr Asn Arg Ala Ser Arg Leu Met Asp Asp Leu
705                 710                 715                 720
```

```
Glu Arg Asn Gln Val Ile Gly Pro Gln Lys Gly Ser Lys Pro Arg Gln
                725                 730                 735
Val Leu Ile Asp Leu Asn Asn Asp Glu Val
                740                 745
```